United States Patent
Sabini et al.

(10) Patent No.: US 6,681,634 B2
(45) Date of Patent: Jan. 27, 2004

(54) BEARING DEFECT DETECTION USING TIME SYNCHRONOUS AVERAGING (TSA) OF AN ENVELOPED ACCELEROMETER SIGNAL

(75) Inventors: Eugene P. Sabini, Skaneateles, NY (US); Jerome A. Lorenc, Seneca Falls, NY (US); Oakley Henyan, Auburn, NY (US); Kenneth L. Hauenstein, Seneca Falls, NY (US)

(73) Assignee: ITT Manufacturing Enterprises, Inc., Wilminington, DE (US)

( * ) Notice: Subject to any disclaimer, the term of this patent is extended or adjusted under 35 U.S.C. 154(b) by 26 days.

(21) Appl. No.: 10/014,044

(22) Filed: Dec. 11, 2001

(65) Prior Publication Data

US 2003/0106375 A1 Jun. 12, 2003

(51) Int. Cl.[7] .................... G01M 13/04; G01N 29/14
(52) U.S. Cl. ................................. 73/593; 73/660
(58) Field of Search .................... 73/660, 659, 658, 73/661, 593

(56) References Cited

U.S. PATENT DOCUMENTS 3,699,806 A * 10/1972 Weichbrodt ............ 73/593
3,733,892 A * 5/1973 Rennick ............... 73/659
4,872,337 A * 10/1989 Watts et al. ............ 73/162
5,663,894 A * 9/1997 Seth et al. ............. 702/56
6,298,725 B1 * 10/2001 Forrester .............. 73/593
6,526,356 B1 * 2/2003 DiMaggio et al. ....... 702/35

FOREIGN PATENT DOCUMENTS

| JP | 57179625 A | * 11/1982 | G01H/1/00 |
| JP | 60076640 A | * 5/1985 | G01M/19/00 |
| JP | 02222818 A | * 9/1990 | G01H/17/00 |

* cited by examiner

Primary Examiner—Hezron Williams
Assistant Examiner—Rose M. Miller

(57) ABSTRACT

A method is provided of identifying a rotating bearing defect featuring the steps of measuring the vibration of the rotating bearing to obtain a waveform signal; filtering the waveform signal to remove unwanted signal frequencies; enveloping the filtered waveform signal to obtain an enveloped low frequency time waveform; and synchronizing the enveloped low frequency time waveform to the running speed of the rotating bearing in such a way to preserve the phase relationship between the tachometer pulse and bearing defect to obtain a time synchronized waveform. The method may include the step of measuring the rotational speed of the rotating bearing; and the step of measuring the rotational speed of the rotating bearing comprises measuring the rotational speed of the rotating bearing with a tachometer.

18 Claims, 2 Drawing Sheets

BEARING DEFECT DETECTION USING TIME SYNCHRONOUS AVERAGING (TSA) OF AN ENVELOPED ACCELEROMETER SIGNAL

FIELD OF THE INVENTION

The invention relates to rotating element bearings, and, more particularly, to methods and devices for identifying rolling element bearing defects.

BACKGROUND OF THE INVENTION

Prior Art

There are several processes used to identify a rolling element bearing defect. Some of the more common methods include (1) comparing a spectrum of vibration measurements with known bearing fault frequencies, (2) measuring and trending high frequency acoustic bearing noise, and (3) analyzing the modulation of an accelerometers natural frequency induced by bearing defects.

In accordance with the first known method, vibration measurements are displayed in either acceleration (g's) or velocity (inches/second). A spectrum of either measurement is generated and investigated to determine if any known bearing fault frequencies are present. Vibration measurements displayed in either acceleration or velocity have one major shortcoming. The known bearing fault frequency amplitude levels are extremely small compared to other rotating equipment vibration levels such as unbalance, misalignment, cavitation, and vane pass. The bearing fault frequency signals are often lost in more predominant vibration signatures.

Measuring and trending of high frequency acoustic noise coming from a bearing housing can also provide an indication of bearing defects. This is because the amount of high frequency acoustic bearing noise will increase as a bearing deteriorates, thereby indicating a deteriorating bearing condition. Measurement of high frequency acoustic noise is a very sensitive way to measure bearing faults. The drawback with this type of bearing detection measurement method is that there are other sources of high frequency acoustic noise found in centrifugal pumps. Pump cavitation, pump recirculation, dry running seals, rubbing laby seals, and pump-motor coupling interference can all be a source of high frequency acoustic noise.

Measuring an accelerometers natural frequency can also provide an indication of a bearing defect. Portable vibration equipment is employed to measure items such as, Spike Energy, HFD, and Peak View. Each of these approaches utilizes the concept whereby the impacts from bearing defects excite the natural frequency of the attached accelerometer. Digital signal processing monitors the excited accelerometer's natural frequency. That signal can be either displayed as an overall level or further analyzed. Further analysis of the excited natural frequency of the accelerometer involves filtering, enveloping and spectrum analysis to detect the presence of any of the known bearing defect frequencies. Bearing defect frequencies are obtained using the physical dimensions of the bearing and established equations.

As is well known in the art, early indications of bearing problems produce frequencies ranging from 250 to 350 kHz. As the wear on the bearing increases, the frequencies drop to around 20 to 60 kHz (1.2M to 3.6M CPM). It is well known in the art how to measure these frequencies, as well as the equations which solve for the frequencies that are involved. In later stages, the bearing defects began to ring at the natural frequencies of the bearing which occur in the range of 30 k to 120 k CPM. The wearing of bearings result in defects which can be expressed in terms of changes in frequency. One can then detect such frequencies as well as harmonics of such frequencies to provide data on bearing life.

There are many publications which describe this, including a publication provided by the Technical Associates of Charlotte, Inc., Copyright 1994 and showing equations as well as other data showing spectral and frequency responses relating to bearing defects. This publication has number R-0894-4 and is incorporated herein by reference.

Measuring the accelerometer's natural frequency has some appealing advantages. The natural frequency of a typical accelerometer is about 20–40 kHz. First, it uses the Accelerometer's Amplification Factor at its natural frequency as a built in amplifier of very low amplitude bearing defect frequencies. Second, filtering out low frequency signals (typically 5000 hertz and below) eliminates the traditional high amplitude pump/impeller generated frequencies such as 1×pump speed and vane pass frequency. Third, the enveloping process transposes a high frequency signal into a time wave form containing only low frequency signals that are easily detectable using standard vibration analysis digital signal processing. A drawback of this system is that it contains a lot of noise that results in a high spectrum noise base. This high-level noise base can easily mask or conceal the bearing defect frequencies.

SUMMARY OF THE INVENTION

This invention combines the advantages of measuring accelerometer signals with Time Synchronous Averaging (TSA) of the accelerometer signals to remove all the vibration frequencies that are not synchronized to the rotational speed of a rotating pump or other rotating equipment. Digital-signal processing is employed that further reduces the electrical noise thereby further reducing the spectrum noise base.

According to one inventive aspect, a method of identifying a rotating bearing defect includes the steps of: measuring an accelerometer signal generated at least in part by the rotating bearing to obtain a waveform signal; filtering the waveform signal using a bandpass filter to remove unwanted signal frequencies; enveloping the filtered waveform signal to obtain an enveloped low frequency time waveform; measuring the rotational speed of the rotating bearing; synchronizing the enveloped low frequency time waveform to the rotational speed of the rotating bearing and the repetitive phase relationship between trigger and bearing defect to obtain a time synchronized waveform; averaging the time synchronized waveform with at least one previously stored time synchronized waveform to obtain an average time synchronized waveform (TSA); spectrum analyzing the TSA; and identifying an amplitude of the TSA at rotating bearing defect frequencies and their multiples.

BRIEF DESCRIPTION OF THE DRAWINGS

Other aspects, advantages and novel features of the invention will become more apparent from the following detailed description of the invention when considered in conjunction with the accompanying drawings wherein.

DETAILED DESCRIPTION

Figure 1:
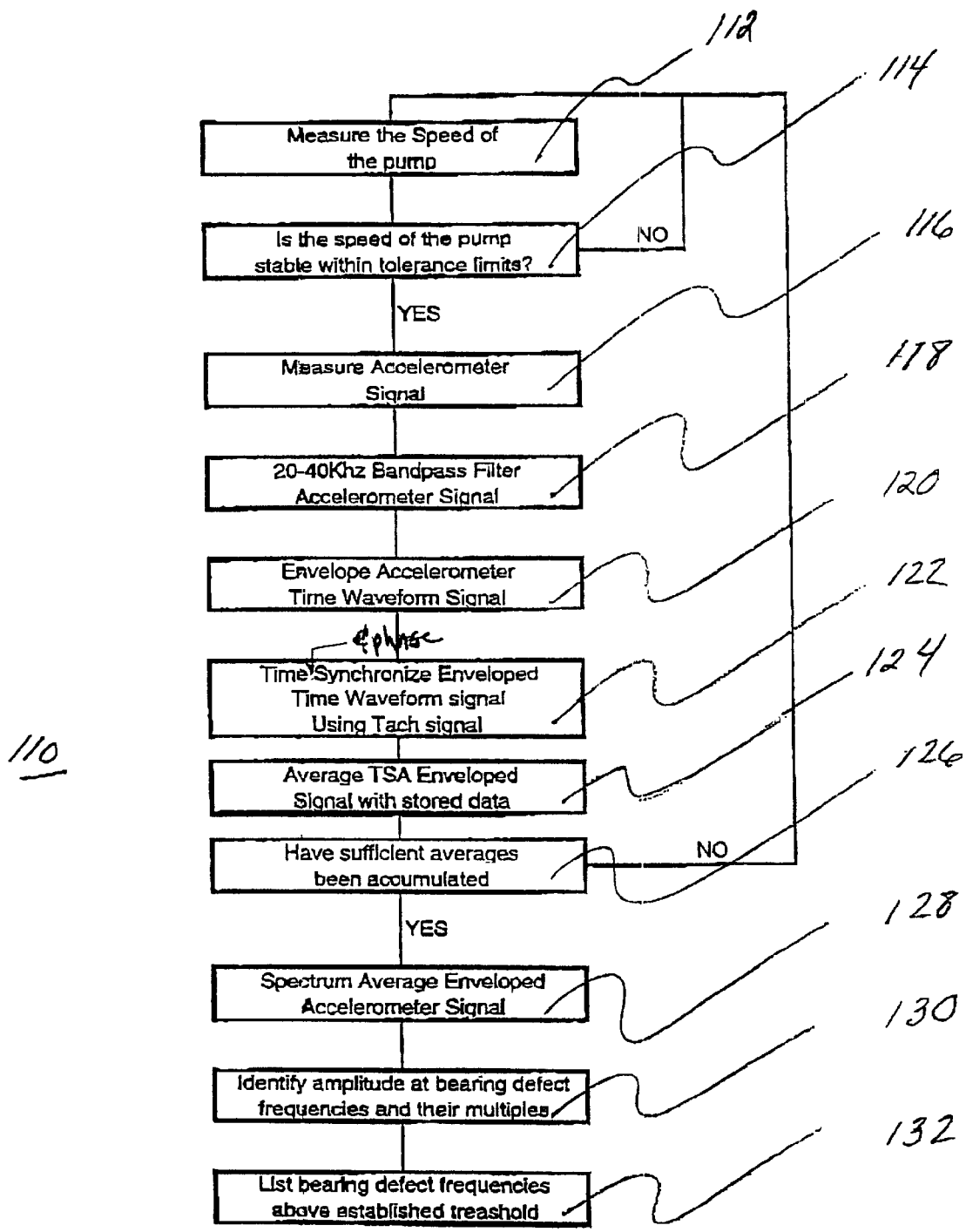
FIG. 1 is a flow chart of the steps involved in identifying rotating bearing defects in accordance with the invention.

Referring to the flow chart 110 shown in FIG. 1, the method of detecting rotating bearing defects, for example, in a rotating pump, is initiated by measuring the rotational speed of the pump (step 112). The measurement of rotational speed can be accommodated by the use of a tachometer. An electric tachometer provides an output voltage or signal that is proportional to speed. Tolerance limits are set based on the desired amount of accuracy. The pump speed is then measured again and compared to the initial measurement to ensure it is stable within the accepted limits (step 114). If the speed is stable the accelerometer signal is measured (step 116). The measured signal, which provides a sampling of vibration amplitudes over time, is known as a time waveform acceleration signal. The first analysis done on the time waveform acceleration signal is to band pass filter the signal centered about the natural frequency of the accelerometer (step 118), usually about 30 kHz.

Next the filtered acceleration time waveform signal is enveloped using either the Hilbert transform function or some other time signal smoothing technique (step 120). This converts the high natural frequency impacts of the accelerometer to a low frequency time wave form that contains the implacts that cause the accelerometer natural frequency to resonate. This enveloped time waveform signal is then synchronized to the running speed of the pump itself in such a way to preserve the phase relationship between the tachometer pulse and bearing defect (step 122). For example, if one of the bearing defect frequency is at 1.5 times the pump running speed the TSA is then synchronized to take place on every other triggered revolution thereby preserving the phase relationship between the trigger and the bearing defect. Techniques for synchronizing a frequency to a rotational speed generated by a tachometer is well known. Once synchronized the time waveform signal is averaged with previous enveloped time synchronized waveforms (unless it is the first waveform where it is simply stored for averaging with subsequent waveforms) (step 124). This procedure is repeated (steps 112–124) until a sufficient number of signal samplings have been averaged (step 126) to obtain a Time Synchronous Average (TSA) of the enveloped time waveform signal.

The completed TSA of the enveloped acceleration signal is processed through a spectrum analyzer to obtain the frequency content of the impacts (step 128) using state of the art FFT Analysis techniques. Amplitudes at known bearing defect frequencies and their multiples are identified (step 130). If the frequency of the impacts can be associated with the bearing fault frequencies, and their amplitude is above an established threshold, a defect in that part of the bearing exists (step 132).

Figure 2:
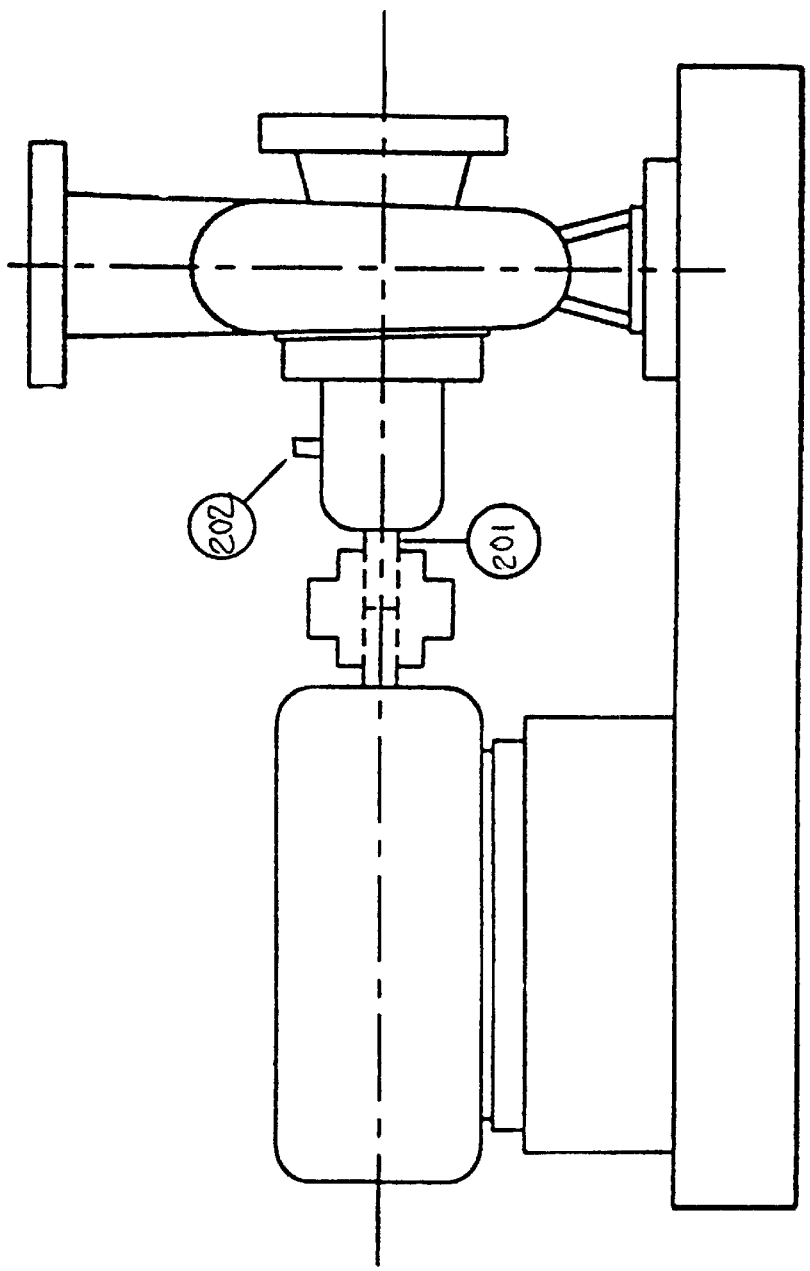
FIG. 2 is a schematic of an end suction pump associated with a tachometers and accelerometer.

FIG. 2 shows a typical end suction pump p with tachometer pickup located at the pump shaft (201) and the accelerometer (202) located on top, vertical position on the bearing housing. Signal filtering eliminates all of the mechanically induced high amplitude, low frequency signals and improves the signal to noise ratio.

It will be understood by those skilled in the art that the foregoing invention is not limited to pump applications. The methods described herein may be applied to any rotating piece of equipment having rolling bearing elements.

Several advantages are achieved in accordance with the invention. For example, the invention provides an improved method of identifying bearing defects in rotating machinery. Time Synchronous Averaging of enveloped accelerometer signals is employed to remove vibration frequencies that are not synchronized to the rotation speed of the rotating pump or other rotating equipment. Thus, the method filters out accelerometer signals that are not attributable to a rotating bearing defect. Further, the invention allows for repeatable trending of equipment bearing defects once they are identified.

Although the invention has been described in terms of exemplary embodiments, it is not limited thereto. Rather, the appended claims should be construed broadly, to include other variants and embodiments of the invention which may be made by those skilled in the art without departing from the scope and range of equivalents of the invention.

What is claimed is:

1. A method of identifying a rotating bearing defect comprising the steps of:
    measuring a rotational speed of a rotating bearing;
    measuring a vibration of the rotating bearing to obtain a waveform signal;
    filtering the waveform signal to remove unwanted signal frequencies;
    enveloping a filtered waveform signal to obtain an enveloped low frequency time waveform; and
    synchronizing the enveloped low frequency time waveform to the running speed of the rotating bearing in such a way to preserve a phase relationship between a tachometer pulse and bearing defect to obtain a time synchronized waveform.

2. The method of claim 1 wherein the step of measuring the rotational speed of the rotating bearing comprises measuring the rotational speed of the rotating bearing with a tachometer.

3. The method of claim 1 wherein the step of measuring the vibration of the rotating bearing comprises measuring the vibration generated at least in part by the rotating bearing using an accelerometer.

4. The method of claim 3 wherein the bandpass filter filters about the natural frequency of the accelerometer.

5. The method of claim 1 wherein the step of filtering the waveform signal comprises filtering the waveform signal using a bandpass filter.

6. The method of claim 1 further comprising the step of storing the time synchronized waveform in a database.

7. The method of claim 6 further comprising the step of averaging the time synchronized waveform with at least one previously stored time synchronized waveform to obtain an average time synchronized waveform (TSA).

8. The method of claim 7 further comprising the step of spectrum analyzing the TSA.

9. The method of claim 8 further comprising the step of identifying an amplitude of the TSA at rotating bearing defect frequencies and their multiples.

10. The method of claim 8 further comprising the step of identifying bearing defect frequencies above a threshold.

11. The method of claim 1 further comprising the step of determining whether the rotational speed of the rotating bearing is within a predetermined range.

12. A method of identifying a rotating bearing defect comprising the steps of:
    measuring a vibration generated at least in part by the rotating bearing using an accelerometer to obtain a waveform signal;
    filtering the waveform signal using a bandpass filter to remove unwanted signal frequencies;
    enveloping the filtered waveform signal to obtain an enveloped low frequency time waveform;
    measuring the rotational speed of the rotating bearing;

synchronizing the enveloped low frequency time waveform to the rotational speed of the rotating bearing in such a way to preserve the phase relationship between the tachometer pulse and bearing defect to obtain a time synchronized waveform;

averaging the time-synchronized waveform with at least one previously stored time synchronized waveform to obtain an average time synchronized waveform (TSA);

spectrum analyzing the TSA; and identifying an amplitude of the TSA at rotating bearing defect frequencies and their multiples.

13. A method for identifying defects in a rolling bearing, comprising the steps of:

measuring a rotational speed of a rolling bearing;

measuring a vibration generated by said rolling bearing using an accelerometer for generating an accelerometer signal, time synchronous averaging said accelerometer signal to remove vibration frequencies which are not in synchronism to the rotational speed of said rolling bearing:

analyzing an averaged signal to obtain bearing defect frequencies indicative of the extent of a bearing defect.

14. The method according to claim 13 further including the steps of:

filtering said accelerometer signal prior to the step of time synchronous averaging to remove unwanted signal frequencies.

15. The method according to claim 14 further including the step of providing an envelope signal from a filtered signal.

16. The method according to claim 15 further including the step of synchronizing a rotational speed signal with said envelope signal.

17. The method according to claim 15 wherein the step of providing an envelope signal includes processing said filtered signal by a signal smoothing technique to provide said envelope signal.

18. The method according to claim 17 wherein said signal smoothing technique employs a Hilbert transform.

* * * * *